US006251092B1

(12) United States Patent
Qin et al.

(10) Patent No.: US 6,251,092 B1
(45) Date of Patent: Jun. 26, 2001

(54) DEFLECTABLE GUIDING CATHETER

(75) Inventors: Jay J. Qin; Duane Dickens, both of Fremont; Laurent Schaller, Los Altos, all of CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/001,249

(22) Filed: Dec. 30, 1997

(51) Int. Cl.[7] .................................................. A61M 31/00
(52) U.S. Cl. ........................ 604/95.01; 604/524; 604/526
(58) Field of Search .............................. 606/32; 604/523, 604/264, 530, 528, 532, 95, 524–527, 95.01; 138/103, 120, 124, 132

(56) References Cited

U.S. PATENT DOCUMENTS

| | | | |
|---|---|---|---|
| 4,586,923 | 5/1986 | Gould et al. | 604/95 |
| 4,748,969 | 6/1988 | Wardle | 128/4 |
| 4,898,577 | 2/1990 | Badger et al. | 604/53 |
| 4,906,230 | 3/1990 | Maloney et al. | 604/95 |
| 4,920,980 | 5/1990 | Jackowski | 128/786 |
| 4,960,134 | 10/1990 | Webster, Jr. | 128/786 |
| 5,114,414 * | 5/1992 | Bachbinder | 604/95 |
| 5,190,050 * | 3/1993 | Nitzsche | 128/772 |
| 5,242,441 | 9/1993 | Avitall | 606/41 |
| 5,318,525 | 6/1994 | West et al. | 604/95 |
| 5,318,526 | 6/1994 | Cohen | 604/95 |
| 5,327,905 | 7/1994 | Avitall | 128/772 |
| 5,334,169 * | 8/1994 | Brown et al. | 604/282 |
| 5,354,297 | 10/1994 | Avitall | 606/45 |
| 5,368,564 * | 11/1994 | Savage | 604/95 |
| 5,431,168 | 7/1995 | Webster, Jr. | 128/658 |
| 5,462,527 * | 10/1995 | Stevens-Wright et al. | 604/95 |
| 5,472,017 | 12/1995 | Kovalcheck | 138/103 |
| 5,487,757 | 1/1996 | Truckai et al. | 607/122 |
| 5,489,270 | 2/1996 | van Erp | 604/95 |
| 5,545,200 * | 8/1996 | West et al. | 607/122 |
| 5,562,619 | 10/1996 | Mirarchi et al. | 604/95 |
| 5,571,085 * | 11/1996 | Accisano, III | 604/95 |
| 5,624,397 * | 4/1997 | Snoke et al. | 604/95 |
| 5,642,736 | 7/1997 | Avitall | 128/772 |
| 5,662,606 * | 9/1997 | Cimino et al. | 604/95 |
| 5,702,373 * | 12/1997 | Samson | 604/282 |
| 5,807,249 * | 9/1998 | Qin et al. | 600/374 |
| 5,820,592 * | 10/1998 | Hammerslag | 604/95 |
| 5,823,955 * | 10/1998 | Kuck et al. | 600/374 |
| 5,882,333 * | 3/1999 | Schaer et al. | 604/95 |
| 5,891,114 * | 4/1999 | Chien et al. | 604/282 |
| 5,897,529 * | 4/1999 | Ponzi | 604/95 |
| 5,951,539 * | 9/1999 | Nita et al. | 604/526 |
| 5,971,975 * | 10/1999 | Mills et al. | 604/527 |

FOREIGN PATENT DOCUMENTS

| | | |
|---|---|---|
| 0 630 657 | 12/1994 | (EP) . |
| 0 815 895 | 1/1998 | (EP) . |
| WO 95/05771 | 3/1995 | (WO) . |

* cited by examiner

*Primary Examiner*—Richard K. Seidel
*Assistant Examiner*—Cris Rodriguez
(74) *Attorney, Agent, or Firm*—Beth L. McMahon (57) ABSTRACT

A deflectable guiding catheter generally having an elongated shaft with a deflectable distal section, a second lumen, a first lumen in fluid communication with a port in the distal end of the shaft, an elongated tapered deflection line within the second lumen, and reinforcement strands within a wall of the shaft. The first lumen is independent from the second lumen, and is therefore not obstructed by the deflection line. The longitudinal axes of the second lumen and first lumen are axially aligned with respect to one another, and are eccentric to the shaft longitudinal axis. The reinforcement strands and the deflection line extend in at least a portion of the deflectable distal shaft section to a location spaced proximally of the distal end of the deflectable distal shaft section.

21 Claims, 7 Drawing Sheets

DEFLECTABLE GUIDING CATHETER

BACKGROUND OF THE INVENTION

The invention relates to the field of intraluminal catheters, and more particularly to a guiding catheter having a deflectable distal end.

Guiding catheters are used in many percutaneous intravascular procedures to guide diagnostic and therapeutic devices or fluids, and the like, to a desired location within the patient. For example, a guiding catheter is typically used in conjunction with balloon catheters used in angioplasty procedures and electrophysiology (EP) devices used for ablation or mapping of cardiac tissue. U.S. Pat. No. 5,509,411, incorporated by reference (Littmann et al.) is an example of an EP catheter.

In the design of guiding catheters, different and often competing considerations relating to catheter flexibility and strength must be balanced. The guiding catheter proximal section must have sufficient flexibility and strength to be advanceable and torqueable, and have sufficient column strength to limit shaft buckling. The distal end of the guiding catheter is typically more flexible than the proximal section, to provide maneuverability and to prevent trauma to the patient's vasculature. However, the distal end must have sufficient strength to prevent kinking during advancement.

While a large delivery lumen is desirable for delivering devices such as EP catheters, the outer diameter of the catheter must be minimized so that the catheter can be readily advanced within the patient. Therefore, when the catheter contains a large delivery lumen, the walls of the catheter are necessarily thin in order to minimize the outer diameter of the guiding catheter. Typically, a tubular or braided metal line reinforcement may be provided within a wall of the catheter. The line reinforcement stiffens the catheter and transmits torque to the catheter distal end as the proximal end of the catheter outside the patient is rotated.

The distal end of the guiding catheter frequently needs to be bent or shaped while within the patient. The bent shape is useful in guiding the catheter distal end into a desired body lumen or chamber. For example, during an EP ablation or mapping procedure, the guiding catheter must be maneuvered through a patient's branched vasculature to advance an EP device into a patient's coronary sinus. Moreover, the shaped or shapeable distal end of the guiding catheter is used to orient the distal tip of the EP device with respect to tissue, such as a patient's endocardium, to facilitate proper delivery of the device's RF or laser energy to the tissue. Consequently, the guiding catheter may be provided with a preformed distal tip which may be guided into the desired location in the patient by rotating the proximal end of the guiding catheter from outside the patient. Additionally, the guiding catheter may be provided with a deflection mechanism to reversibly deflect the distal tip while within the patient.

One difficulty has been providing a deflectable guiding catheter having sufficient column strength and torque transmission in combination with a relatively large lumen for delivering devices such as EP catheters. Moreover, many prior deflectable catheters are typically limited to uniplanar deflection, which requires the catheter shaft to be rotated from its proximal end located outside of the patient in order to place to deflected tip into a desired plane, as, for example, to place the distal tip of the catheter into a desired branched vessel or in contact with a desired tissue wall.

What has been needed is a catheter with a kink resistant, torqueable, and deflectable shaft which nonetheless defines a large unobstructed lumen for receiving a device therein. The present invention satisfies these and other needs.

SUMMARY OF THE INVENTION

The invention is directed to a catheter comprising an elongated shaft which has a deflectable distal section and an unobstructed delivery lumen, with kink resistance and torque transmission.

The guiding or delivery catheter of the invention generally has an elongated shaft with a deflectable distal section, a deflection line lumen, and a delivery lumen in fluid communication with a port in the distal end of the shaft. An elongated, preferably tapered, deflection line is disposed within the deflection line lumen. Preferably the wall of the shaft has reinforcing or stiffening strands or fibers which may be braided or wound. The longitudinal axes of the deflection line lumen and delivery lumen are axially aligned with respect to one another, and are eccentric to the central longitudinal axis of the shaft. The phrase "axially aligned" refers to the fact that the two lumens are aligned along a bisecting plane intersecting the central longitudinal axis of the shaft.

To selectively deflect the shaft distal section, the operator moves the deflection line longitudinally. From an undeflected position aligned with the shaft longitudinal axis, the distal shaft section is deflected away from the shaft longitudinal axis by pulling the line proximally out the proximal end of the shaft. In one embodiment, if the deflection line is stiff enough, the deflection line may be moved longitudinally toward the distal end of the shaft to deflect the shaft distal section in an opposite direction. In one example, the catheter is provided with a steering mechanism on the catheter proximal end, which facilitates the longitudinal movement of the deflection line by the operator.

The catheter of the invention is kink resistant and torqueable. The deflection line, which extends to the distal end of the deflection line lumen, provides column strength and is tapered to provide a smooth transition of stiffness from the catheter proximal shaft section to the deflectable distal shaft section. The distal end of the deflection line lumen extends into at least a portion of the deflectable distal shaft section to a location spaced proximally from the distal end of the deflectable distal shaft section. The deflection line generally extends in about 70% to about 95%, preferably about 85% to about 90%, of the total length of the deflectable distal shaft section. The distal end of the shaft is provided with improved flexibility due to the deflection line terminating proximal to the distal tip of the shaft.

The shaft is reinforced with suitable reinforcing strands or fibers, such as stiffening wire braids, which contribute to the shaft column strength and torque transmission. The reinforcement extends at least into a portion of the deflectable distal shaft section. Generally the reinforcement extends in about 15% to about 50%, preferably about 25% to about 45% of the total length of the deflectable distal shaft section. The reinforcements are preferably made of stainless steel, although other materials with similar stiffness are suitable, such as NITINOL, MP35N, Elginoy, and high strength polymer materials such as polyamide and Kevlar®.

The delivery lumen of the guiding catheter is independent from, or fluidly sealed from, the deflection line lumen, and thus provides an unobstructed passageway for slidably receiving an EP or other therapeutic or diagnostic agent or device. Because the guiding catheter of the invention provides superior control in accessing desired cardiovascular structure, it is particularly useful in supporting and delivering an EP mapping or ablation catheter to various locations in cardiac chambers for diagnosis or therapy. For example, the guiding catheter of the invention may be advanced into the right atrium of the heart from the inferior vena cava to position the operative distal end of an EP catheter within the right atrium above the tricuspid valve. The electrodes on the distal end of the EP catheter can then be put into operative contact with the cardiac tissue of the right atrium by torquing and/or deflecting the tip of the guiding catheter of the invention. Consequently, where a plurality of electrodes are on the EP device distal end, the range of movement and control of the guiding catheter of the invention allows for all the electrodes to be in contact with the cardiac tissue together, so that a more extensive area may be operatively engaged with the device at a given time. In this manner a continuous lesion may be formed from a plurality of individual ablations.

The guiding catheter of the invention has a deflectable distal shaft section and an unobstructed delivery lumen available for delivering therapeutic and diagnostic devices, yet has sufficient strength to transmit torque and resist kinking. By offsetting the central axes of the two lumens from the shaft longitudinal axis and axially aligning the two lumens, while reinforcing the shaft with the deflection line and line braids, the catheter transmits torque and resists kinking. These and other advantages of the invention will become more apparent from the following detailed description of the invention and the accompanying exemplary drawings.

DETAILED DESCRIPTION OF THE INVENTION

Figure 1:
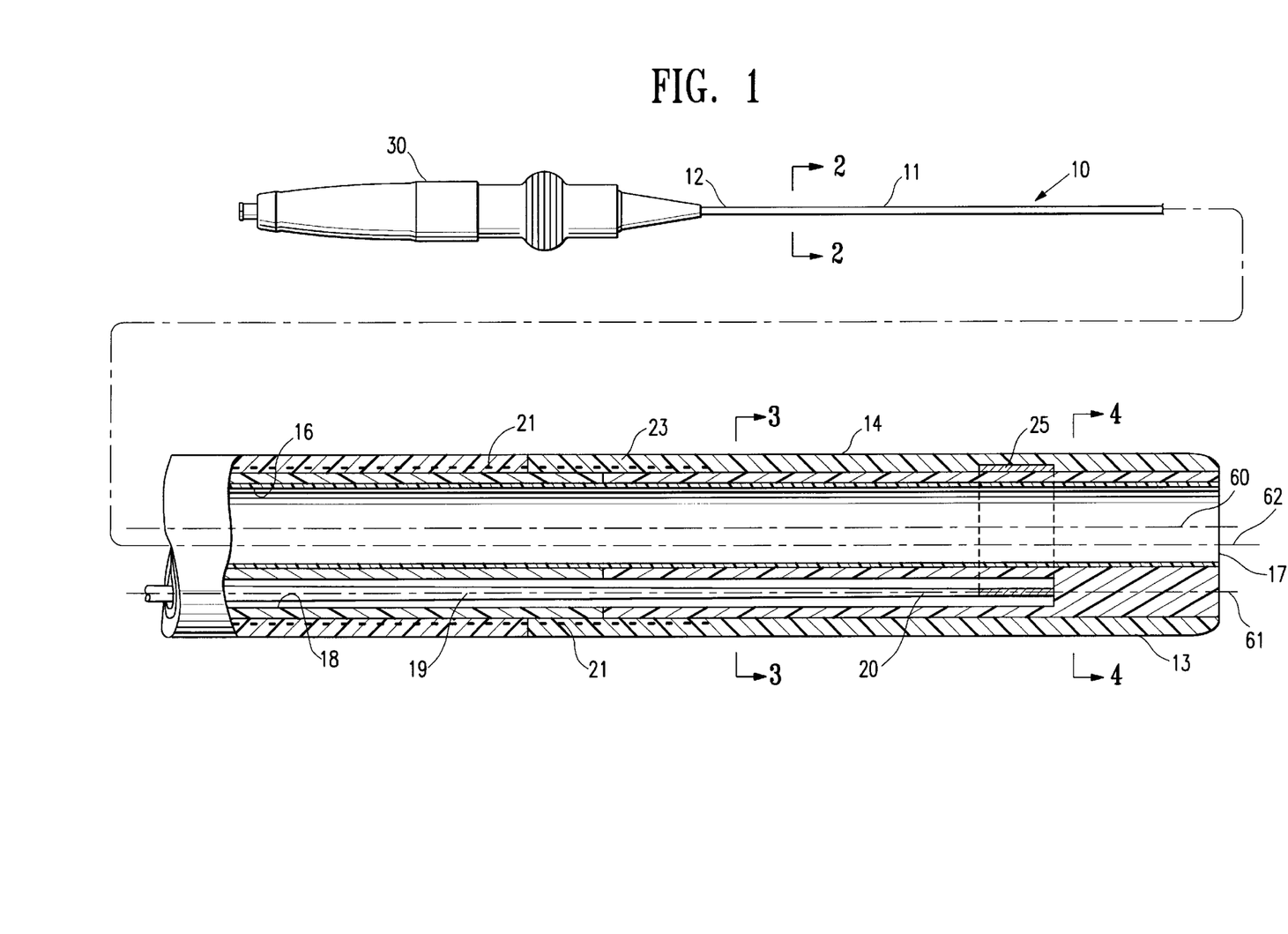
FIG. 1 is a longitudinal view, partially in longitudinal cross-section, of a guiding catheter embodying features of the invention.

FIG. 1 illustrates an embodiment of a guiding catheter 10 of the invention comprising an elongated shaft 11 having a proximal end 12 and a distal end 13 and a deflectable distal shaft section 14. A first lumen 16, located eccentric to the shaft longitudinal axis, extends within the shaft 11 to a port 17 in the shaft distal end 13. A second lumen 18, located eccentric to the shaft longitudinal axis and axially aligned with the first lumen 16, extends to a location proximal to the shaft distal end 13. An elongated deflection line, or member, 19 is received within the second lumen 18, and has a tapered distal section 20 with a radially decreasing diameter. Stiffening wire braids 21, embedded in the shaft 11, reinforce the shaft to provide sufficient column strength and rigidity for shaft kink resistance and torqueability.

Figure 2:
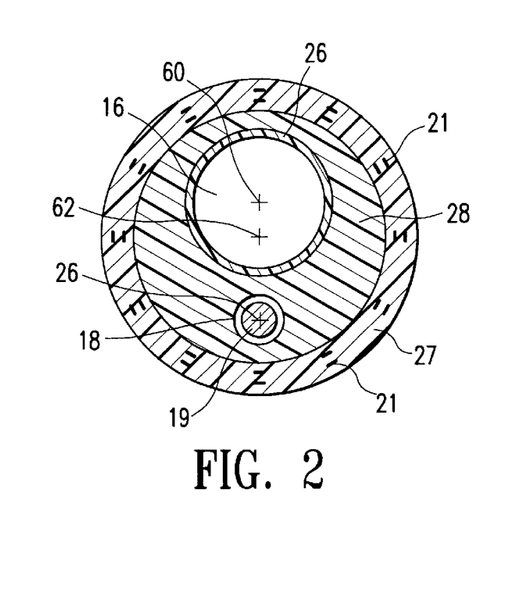
FIG. 2 is a cross section of the catheter shown in FIG. 1 taken along lines 2—2.
Figure 3:
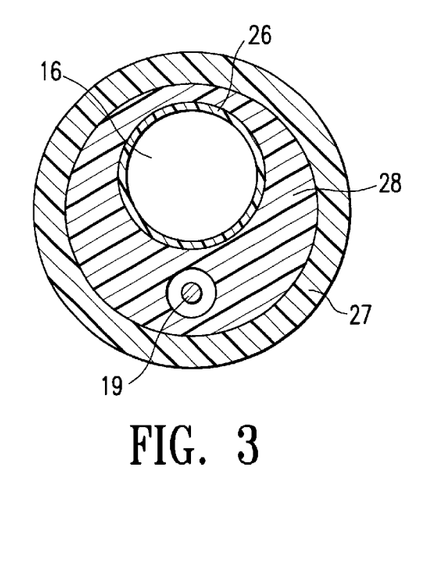
FIG. 3 is a cross section of the catheter shown in FIG. 1 taken along lines 3—3.
Figure 4:
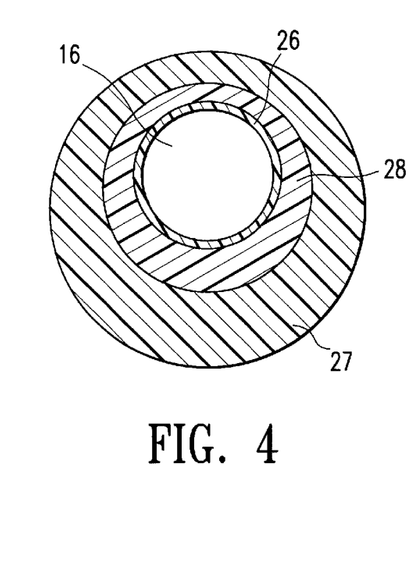
FIG. 4 is a cross section of the catheter shown in FIG. 1 taken along lines 4—4.

In FIG. 1, dashed lines illustrate the location of the axes of the lumens 16, 18 and the axis of the shaft 11. As illustrated in FIGS. 2–4, showing transverse cross sections of the catheter shown in FIG. 1, the first lumen 16 and the second lumen 18 are axially aligned with respect to one another and are eccentric to the shaft longitudinal axis. Thus, the axis 60 of the first lumen 16 and the axis 61 of the second lumen 18 are aligned along a plane intersecting the central axis 62 of the shaft 11. In one embodiment, the first lumen 16 is lined with a liner 26 having a lubricious surface which facilitates advancement of a device slidably received within the first lumen 16. The lubricious liner 26 may be made of fluoropolymer.

The length of the guiding catheter 10 may be about 60 cm to about 120 cm in working length, typically about 80 to about 100 cm for use with an EP catheter. The length of the deflectable distal shaft section 14 is about 5 cm to about 15 cm, preferably about 7 to about 10 cm. The wire braids 21 extend from the proximal end 12 of the shaft 11 and within at least a proximal portion 23 of the deflectable distal shaft section 14, to a location spaced proximally from the shaft 11 distal end 13. In a presently preferred embodiment, the length of the deflectable distal shaft section 14 having wire braids 21 located therein is about 1.0 cm to about 2.5 cm.

The deflection line total length depends on the length of the catheter. The second lumen 18, and deflection line 19 therein, extend from the proximal end 12 of the shaft at least into the deflectable distal shaft section 14 to a location spaced proximally of the distal end of the catheter shaft. In a presently preferred embodiment, the length of the deflection line located within the deflectable distal shaft section 14 is about 4 cm to about 12 cm, preferably about 5 cm to about 10 cm, and the length of the deflection line 19 extending beyond the distal end of the wire braids 21 is about 1.5 cm to about 10 cm, preferably about 2.5 cm to about 7 cm.

The distal end of the deflection line 19 is secured to the catheter shaft 11 at the distal end of the second lumen 18. In the embodiment illustrated in FIG. 1, an annular clamp 25 secures the deflection line 19 to the shaft 11. The deflection line, if formed out of stainless steel wire, has a diameter of about 0.006 inch (0.015 cm) to about 0.015 inch (0.04 cm), preferably about 0.008 inch (0.02 cm) to about 0.012 inch (0.03 cm), which tapers to a smaller diameter at the distal extremity of the line. The length of the tapered distal section 20 is about 6 to about 15 cm, preferably about 8 cm to about 12 cm. The tapered line 19, in conjunction with other features of the invention, provides sufficient column strength that allows the guiding catheter to be deflected in two directions.

The guiding catheter 10 has an outer diameter (OD) of about 5 French (0.17 cm) to about 15 Fr (0.5 cm), preferably about 6 Fr (0.2 cm) to about 12 Fr (0.4 cm). The diameter of the first lumen will be determined by the device to be delivered, and usually should be about 0.010 inch (0.025 cm) larger than the OD of the device to be delivered. The diameter of the first lumen may range from about 0.035 inch (0.09 cm) to about 0.105 inch (0.26 cm), and preferably about 0.045 inch (0.11 cm) to about 0.105 inch (0.26 cm), and is typically about 0.05 inch (0.13 cm) to about 0.08 inch (0.20 cm) for use with an EP catheter.

As best illustrated in FIGS. 2–4, the catheter shaft 11 has a two layer construction, with an outer jacket 27 surrounding a core 28. The outer jacket 27 is preferably a thermoplastic material such as a thermoplastic polyurethane (PU) or PU blend, and the core 28 is preferably a thermoplastic PU or PU blend. While the outer diameter of the shaft 11 is constant, the outer diameter of the core 28 steps down to a smaller diameter at a location distal to the distal end of the second lumen. The outer jacket 27 has a wall thickness of about 0.004 inch (0.01 cm) to about 0.009 inch (0.023 cm), preferably about 0.005 inch (0.013 cm) to about 0.007 inch 0.018cm) in a section of the shaft 11 containing the first lumen 16 and the second lumen 18, and a nonuniform wall thickness of about 0.006 inch (0.015 cm) to about 0.025 inch (0.064 cm) in a section of the shaft located distally from the distal end of the second lumen 18. The core 28 defines the shaft lumens, and has a first diameter of about 0.060 inch (0.15 cm) to about 0.062 inch (0.16 cm) in a section of the shaft 11 containing the first lumen 16 and the second lumen 18, and a second diameter of about 0.014 inch (0.036 cm) to about 0.016 inch (0.04 cm) in a section of the shaft located distally from the distal end of the second lumen 18.

Figure 5:
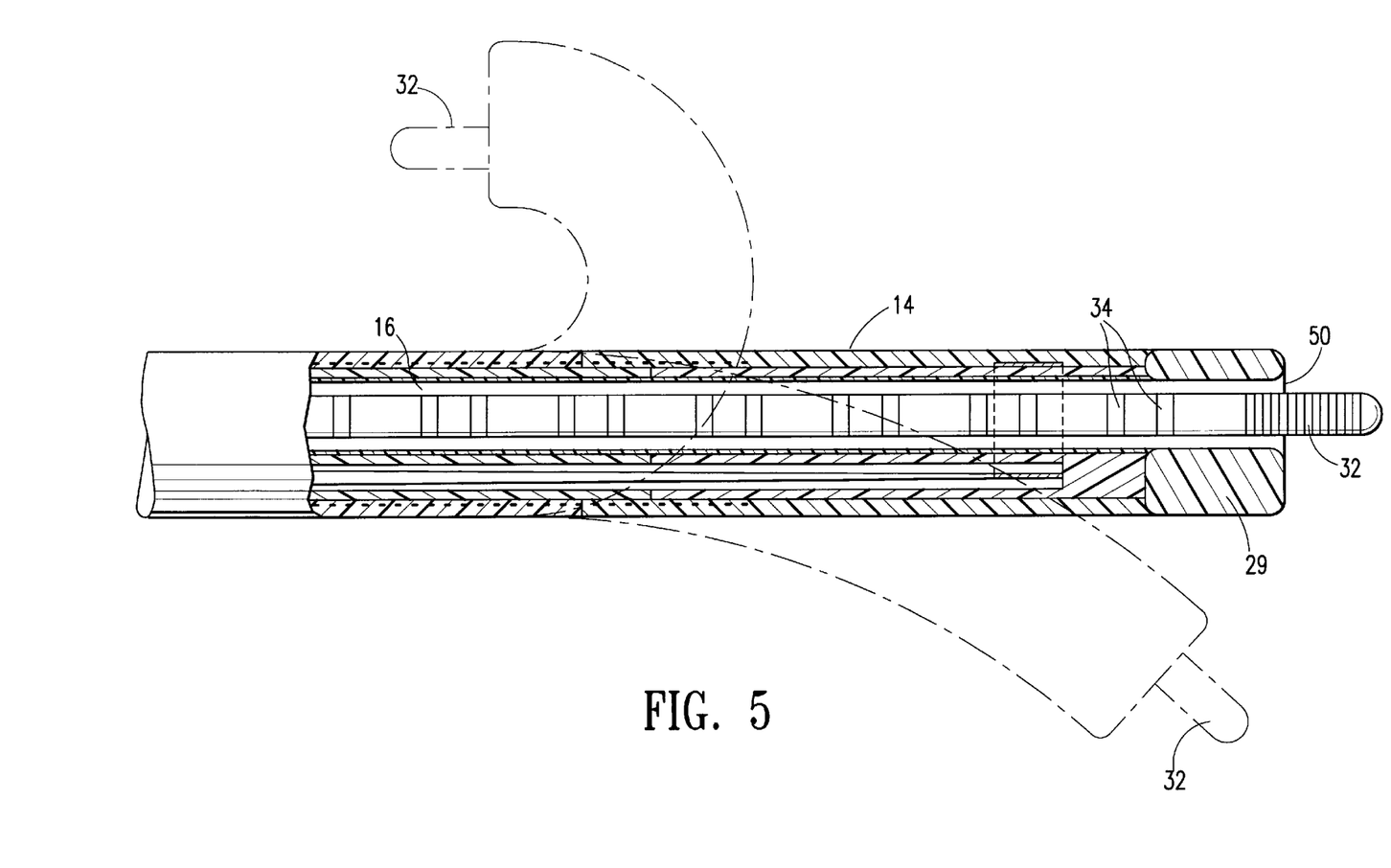
FIG. 5 is a longitudinal view of a catheter of the invention showing the deflection of the distal shaft section, and an EP device located therein.

FIG. 5 illustrates the deflection of the distal shaft section 14 in two opposite directions. In the embodiment illustrated in FIG. 5, EP device 32, having a plurality of electrodes 34, is within the first lumen 16. By deflecting the distal shaft section 14, a diagnostic or therapeutic device in the first lumen 16 can be accurately positioned within the patient.

Figure 6:
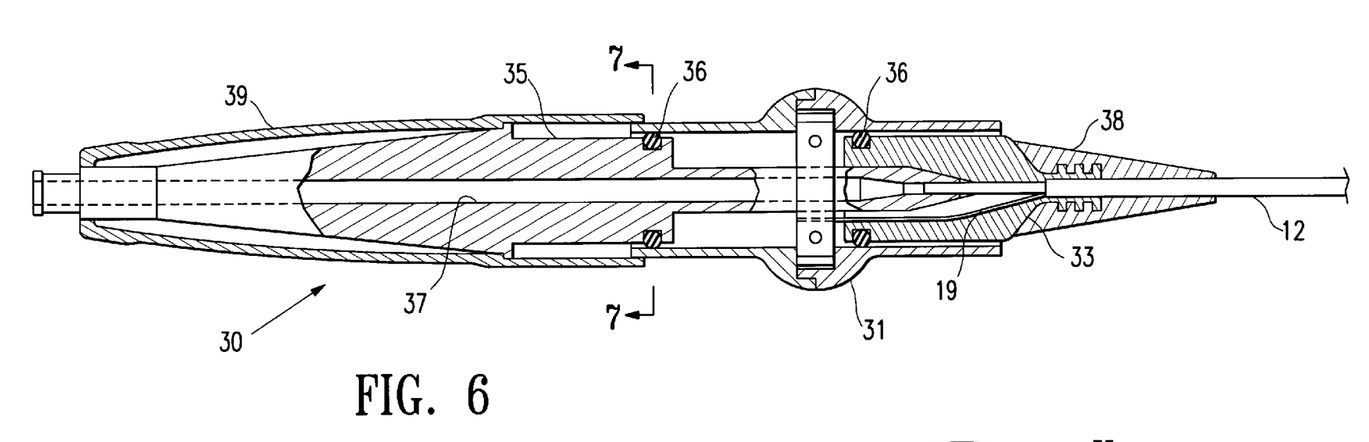
FIG. 6 is a longitudinal view, partially in section, of a handle for use with the catheter of the invention.
Figure 7:
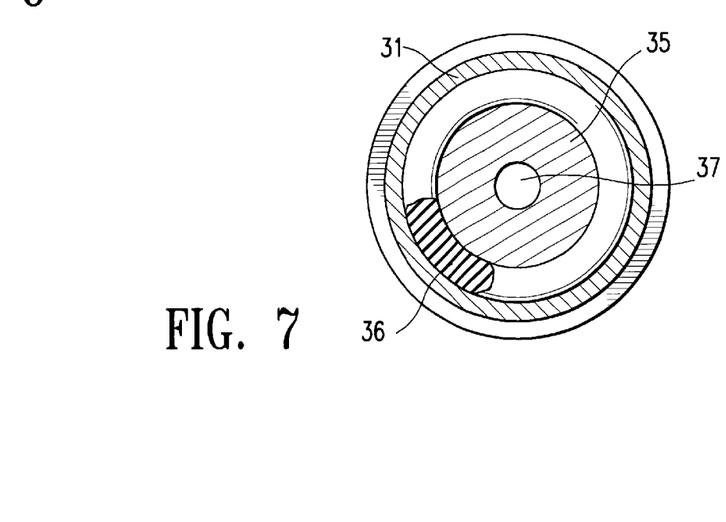
FIG. 7 illustrates a transverse cross section of the handle shown in FIG. 6 taken along lines 7—7.

As illustrated in FIG. 1, a handle 30 may be provided on the proximal end 12 of the shaft 11, with a mechanism for moving the deflection line 19 longitudinally to deflect the distal shaft section 20. A presently preferred embodiment of a handle 30, illustrated in FIG. 6, generally comprises a sliding member 31 slidably disposed about a connecting member 33 and an inner member 35, and one or more o-rings 36 disposed about connecting member 33 and inner member 35. Inner member 35 has a lumen 37 extending therein from a port in the proximal end to a port in the distal end of the inner member. FIG. 7 illustrates a transverse cross-section of the handle shown in FIG. 6, taken along lines 7—7. Connecting member 33 releasably secures the proximal end 12 of the catheter shaft to handle 30. The sliding member 31 secures to the proximal portion of the deflection line 19 by a variety of suitable means including screws, hooks, and clamp connectors, such as clamping plates shown in FIG. 6. The sliding member 31 generally comprises two joined pieces which may be separated to expose the deflection line securing means. When sliding member 31, and the deflection line secured thereto, are longitudinally displaced, the distal shaft section 14 is deflected in either of two opposite directions depending on whether the sliding member is displaced proximally or distally. O-rings 36 between the sliding member 31 and the inner member 35 and connecting member 33 provide a frictional stop on the displacement of the sliding member, so that sliding member 31 can be smoothly displaced when pulled or pushed by the operator but remains set in any deflected position without the need of a separately actuated lock. In the embodiment shown in FIG. 6, the connecting member 33 tapers toward the distal end, and ridges are provided on the distal end for frictional engagement with optional strain relief member 38. Outer member 39, disposed about the inner member 35, provides a comfortable grip for the operator. A radially enlarged finger grip is provided on the sliding member, and may have grooves on an outer surface to improve the operator's grip on the sliding member. The guiding catheter of the invention may be used with other suitable handle configurations. For example, the handle may be provided with a knob which is rotated clockwise to longitudinally move the deflection line 19 in a distal direction toward the distal end of the catheter 10 and counterclockwise to move the deflection line in a proximal direction away from the distal end of the catheter.

Figure 8:
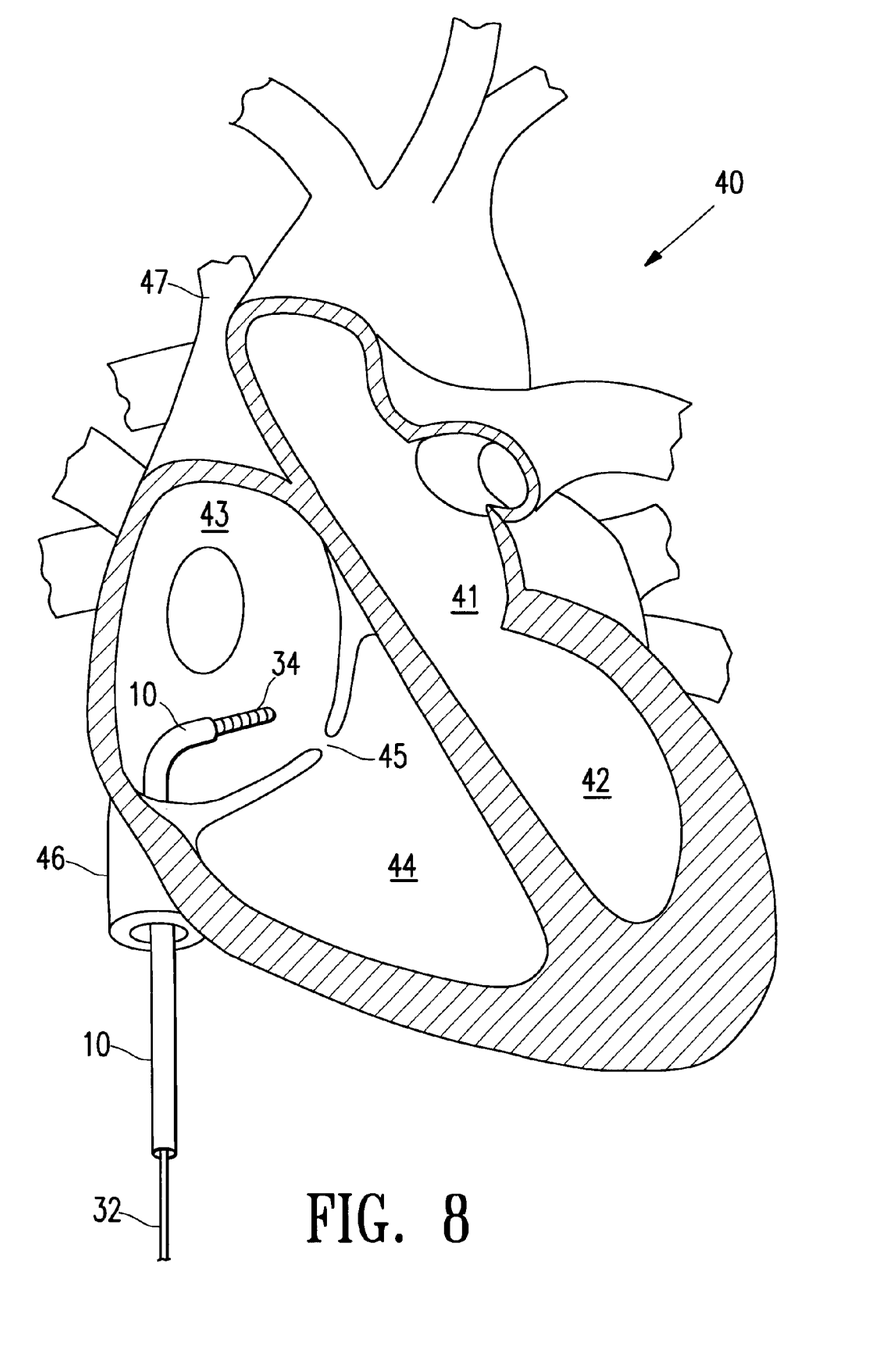
FIG. 8 illustrates a guiding catheter of the invention, and an EP device located therein, positioned in the right atrium of a heart.
Figure 9:
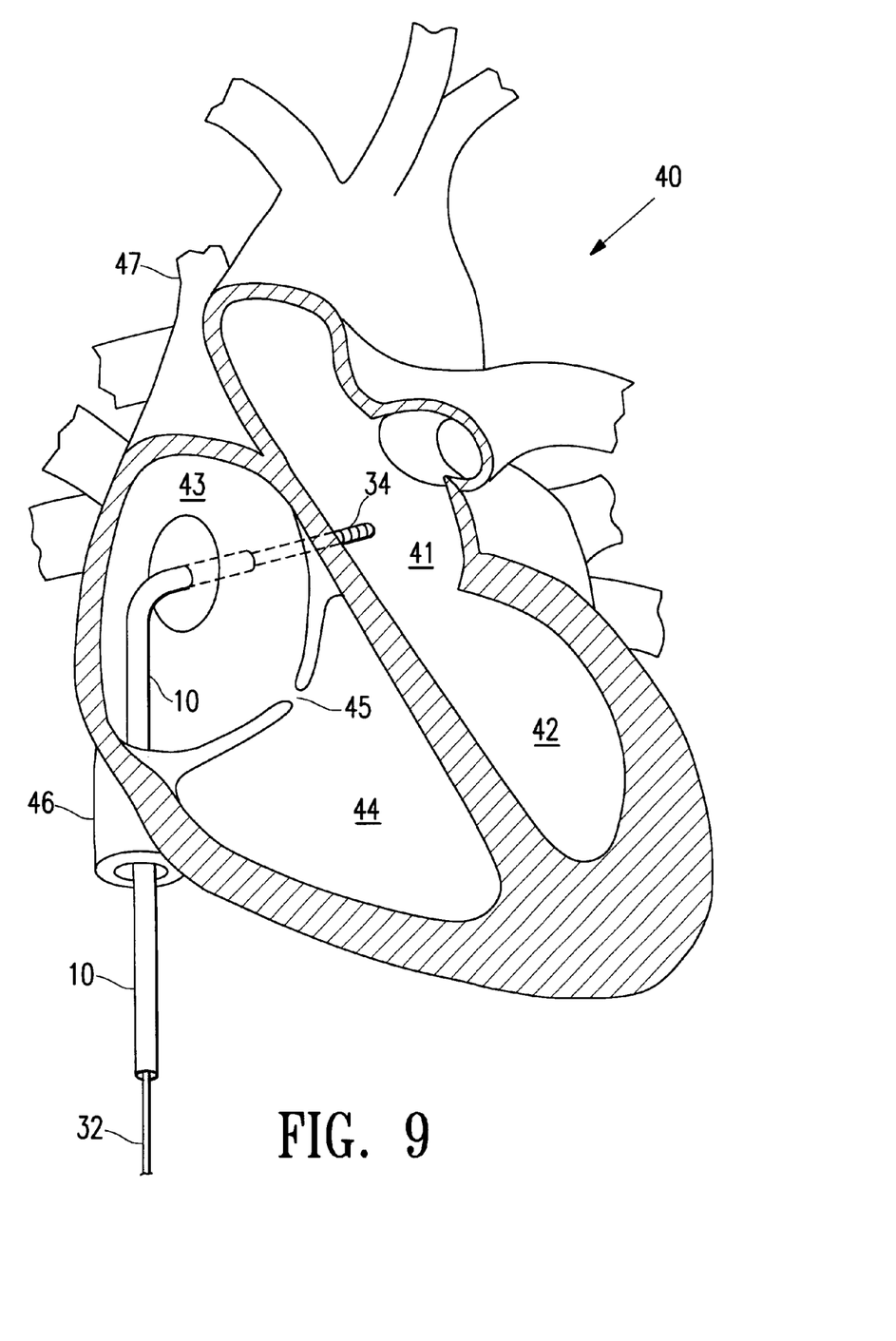
FIG. 9 illustrates a guiding catheter of the invention, and an EP device located therein, in the left atrium of the heart by transseptal insertion.

The range of movement and control provided by the guiding catheter of the invention provides for superior access to desired cardiac structure. FIG. 8 illustrates a heart 40, and the anatomy of the heart including the left atrium 41 and left ventricle 42, and the right atrium 43 and right ventricle 44 separated by the tricuspid valve 45. The inferior vena cava 46 and superior vena cava 47 deliver deoxygenated blood from the body tissues, into the right atrium, from where it is pumped through the tricuspid valve 45 and ultimately into the lungs for reoxygenation. In FIG. 8, the guiding catheter 10, and EP catheter 32 therein, are shown in the inferior vena cava 46 and the right atrium 43 above the tricuspid valve 45. The position of the guiding catheter 10 allows a plurality of the electrodes 34 on the EP catheter 32 distal end to be placed in operative contact with the cardiac tissue of the right atrium 43. FIG. 9 illustrates the distal end of the guiding catheter 10, and EP catheter 32 therein, positioned in the left atrium transseptally through the fossa ovalis.

Figure 10:
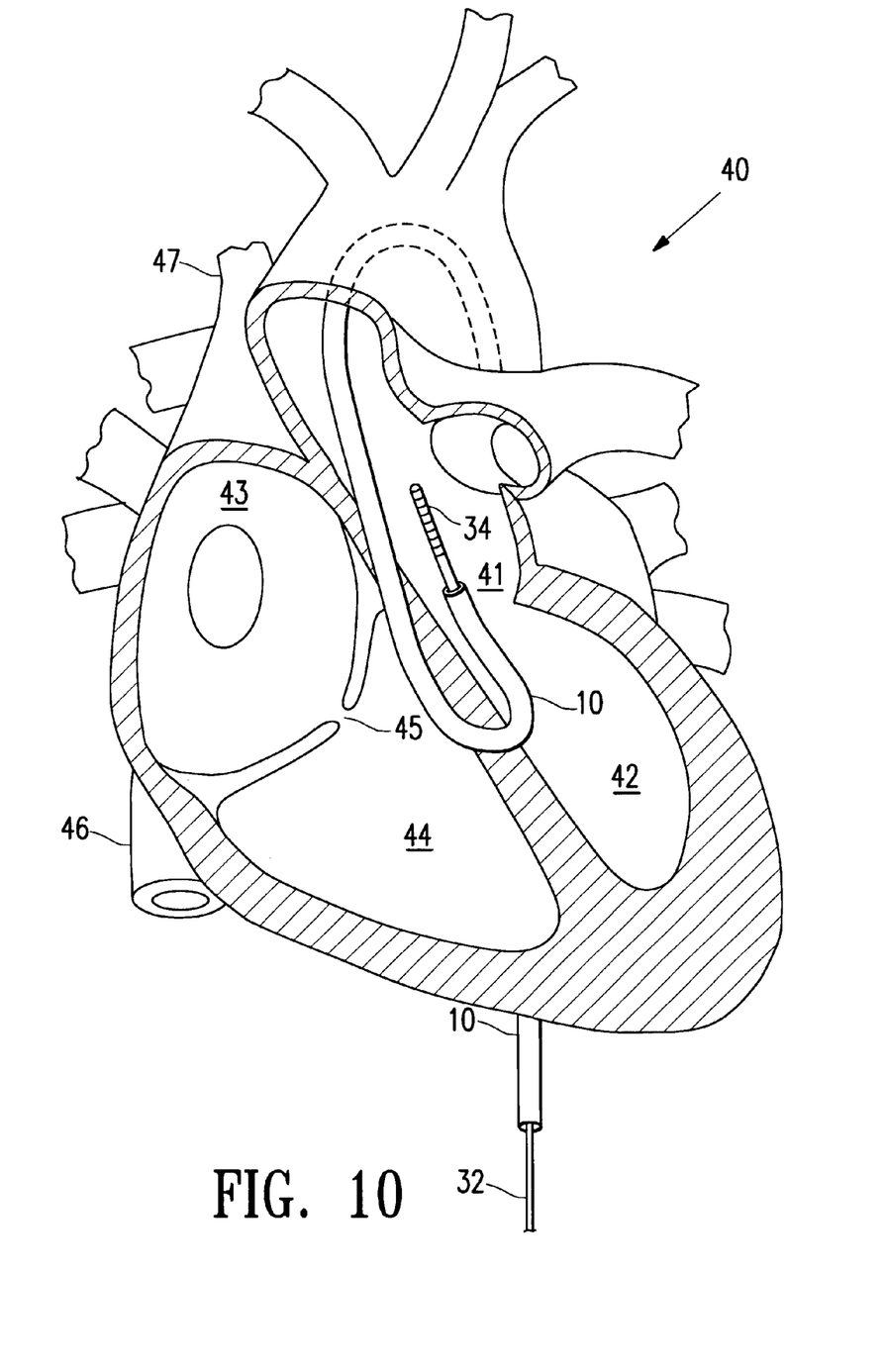
FIG. 10 illustrates a guiding catheter of the invention, and an EP device located therein, in the left atrium by retrograde insertion.

As illustrated in FIG. 10, the guiding catheter can also be advanced into the left cardiac chambers retrogradely through the aortic and mitral valves. FIG. 10 illustrates the operative distal end of the EP catheter positioned in the left atrium, where a distal section of the catheter is shown projecting out of the plane of the figure.

The material used to make the deflectable distal shaft section 14 may be softer or more flexible from the material used in the remainder of the catheter shaft 11. In one embodiment, a soft atraumatic distal tip 29, illustrated in FIG. 5, is provided on the distal end 13 of the shaft, with a lumen 50 and a distal end port in fluid communication with the first lumen 16.

While the present invention has been described herein in terms of certain preferred embodiments, modifications and improvements may be made to the invention without departing from the scope thereof.

What is claimed is:

1. A guiding catheter, comprising,
    a) an elongated catheter shaft having a proximal end, a distal end, a relatively stiff proximal section, a deflectable distal section with at least a length which is relatively more flexible than the relatively stiff proximal section, a longitudinal axis, and reinforcements embedded in the shaft extending from the proximal section to at least a portion of the deflectable distal section;
    b) a first lumen eccentric to the longitudinal axis of the shaft;
    c) a second lumen axially aligned with the first lumen and eccentric to the longitudinal axis;
    d) an elongated deflection member which has proximal and distal ends, which is disposed in the second lumen, and which has the distal end thereof secured to the shaft; and
    e) a soft distal tip on the distal end of the shaft, having a lumen extending therein in fluid communication with the first lumen, and having a port in a distal end of the soft distal tip.

2. The catheter of claim 1 wherein the second lumen extends from the shaft proximal end and within at least a portion of the deflectable distal section to a location spaced proximally from the distal end of the catheter shaft.

3. The catheter of claim 2 wherein the deflectable distal section is about 5 to about 15 cm in length.

4. The catheter of claim 3 wherein the second lumen extends in about 4 to about 12 cm of the length of the deflectable distal section.

5. The catheter of claim 3 wherein the deflection member extends in about 4 to about 12 cm of the length of the deflectable distal section.

6. The catheter of claim 1 wherein the first lumen extends from the shaft proximal end to the shaft distal end.

7. The catheter of claim 1 wherein the reinforcements are wire braids.

8. The catheter of claim 7 wherein the wire braids extend from the proximal end of the shaft to within at least a portion of the deflectable distal section.

9. The catheter of claim 8 wherein the wire braids extend to a location spaced proximally from a distal end of the second lumen.

10. The catheter of claim 9 wherein the wire braids extend in about 1 to about 2.5 cm of the length of the deflectable distal section.

11. The catheter of claim 1 wherein the elongated deflection member has a tapered distal section with a radially decreasing diameter.

12. The catheter of claim 11 wherein the length of the deflection member tapered distal section is about 6 to about 15 cm.

13. The catheter of claim 1 wherein the first lumen has a diameter of about 0.09 to about 0.26 cm.

14. The catheter of claim 1 wherein the catheter diameter is about 0.20 to about 0.40 cm.

15. The catheter of claim 1 wherein the longitudinal axis of the catheter shaft is within the first lumen.

16. The catheter of claim 1 wherein the first lumen is unobsructed.

17. A guiding catheter, comprising,
a) an elongated catheter shaft having a proximal end, a distal end, a longitudinal axis, a relatively stiff proximal section, a deflectable distal section with at least a length which is relatively more flexible than the relatively stiff proximal section, and reinforcements in at least a portion of the shaft;
b) a first lumen eccentric to the longitudinal axis of the shaft;
c) a second lumen axially aligned with the first lumen and eccentric to the longitudinal axis;
d) an elongated deflection member which has proximal and distal ends, which is disposed in the second lumen, and which has the distal end thereof secured to the shaft; and
e) a soft distal tip on the distal end of the shaft, having a lumen extending therein in fluid communication with the first lumen, and having a port in a distal end of the soft distal tip.

18. The guiding catheter of claim 17 wherein the reinforcements in the deflectable distal section comprise wound strands.

19. A guiding catheter, comprising,
a) an elongated catheter shaft having a proximal end, a distal end, a relatively stiff proximal section, a deflectable distal section with at least a length which is relatively more flexible than the relatively stiff proximal section, a longitudinal axis, reinforcements in at least a portion of the proximal shaft section, and reinforcements in at least a portion of the deflectable distal shaft section;
b) a first lumen eccentric to the longitudinal axis of the shaft;
c) a second lumen axially aligned with the first lumen and eccentric to the longitudinal axis;
d) an elongated deflection member which has a proximal end, a distal end, and a tapered distal section with a radially decreasing diameter, which is disposed in the second lumen, and which has the distal end thereof secured to the shaft; and
e) a port on the distal end of the shaft in fluid communication with the first lumen.

20. A guiding catheter, comprising,
a) an elongated catheter shaft having a proximal end, a distal end, a longitudinal axis, a relatively stiff proximal section, a deflectable distal section with at least a length which is relatively more flexible than the relatively stiff proximal section, and reinforcements in at least a portion of the shaft;
b) a first lumen eccentric to the longitudinal axis of the shaft;
c) a second lumen axially aligned with the first lumen and eccentric to the longitudinal axis;
d) an elongated deflection member which has a proximal end, a distal end, and a tapered distal section with a radially decreasing diameter, which is disposed in the second lumen, and which has the distal end thereof secured to the shaft; and
e) a port on the distal end of the shaft in fluid communication with the first lumen.

21. A guiding catheter, comprising,
a) an elongated catheter shaft having a proximal end, a distal end, a relatively stiff proximal section, a deflectable distal section with at least a length which is relatively more flexible than the relatively stiff proximal section, a longitudinal axis, reinforcements in at least a portion of the proximal shaft section, and reinforcements in at least a portion of the deflectable distal shaft section, the deflectable distal shaft section naturally assuming an undeflected position aligned with a longitudinal axis of a shaft section located proximal to the deflectable distal shaft section;
b) a first lumen eccentric to the longitudinal axis of the shaft;
c) a second lumen axially aligned with the first lumen and eccentric to the longitudinal axis;
d) an elongated deflection member which has a proximal end and a distal end, which is disposed in the second lumen, and which has the distal end thereof secured to the shaft; and
e) a soft distal tip on the distal end of the shaft, having a lumen extending therein in fluid communication with the first lumen, and having a port in a distal end of the soft distal tip.

* * * * *

UNITED STATES PATENT AND TRADEMARK OFFICE
CERTIFICATE OF CORRECTION

PATENT NO.     : 6,251,092 B1
DATED          : June 26, 2001
INVENTOR(S)    : Jay J. Qin, Duane Dickens and Laurent Schaller It is certified that error appears in the above-identified patent and that said Letters Patent is hereby corrected as shown below:

<u>Column 7,</u>
Line 34, after the word "catheter" and before the word "diameter" insert -- outer --.

Signed and Sealed this

Eleventh Day of February, 2003

JAMES E. ROGAN
*Director of the United States Patent and Trademark Office*